(12) United States Patent
Swan et al.

(10) Patent No.: US 8,202,833 B2
(45) Date of Patent: Jun. 19, 2012

(54) COMPOSITION CONTAINING BIOCOMPATIBLE POLYMERIZATION ACCELERATOR AND POLYMERIZABLE MATERIAL

(75) Inventors: Dale G. Swan, St. Louis Park, MN (US); Stephen J. Chudzik, St. Paul, MN (US); Ronald F. Ofstead, Maplewood, MN (US)

(73) Assignee: Surmodics, Inc., Eden Prairie, MN (US)

( * ) Notice: Subject to any disclaimer, the term of this patent is extended or adjusted under 35 U.S.C. 154(b) by 817 days.

(21) Appl. No.: 10/723,505

(22) Filed: Nov. 26, 2003

(65) Prior Publication Data

US 2005/0112086 A1   May 26, 2005

(51) Int. Cl.
*A61K 38/00* (2006.01)
*A61K 38/39* (2006.01)
*A61K 31/715* (2006.01)
*A61K 31/727* (2006.01)
*A61K 9/14* (2006.01)
*C12N 11/02* (2006.01)
*C12N 11/04* (2006.01)
*C12N 5/07* (2010.01)
*C07K 17/02* (2006.01)
*C07K 17/04* (2006.01)

(52) U.S. Cl. ........ 514/1.1; 424/93.7; 424/484; 424/488; 435/177; 435/182; 514/17.2; 514/54; 514/55; 514/56; 530/402; 530/812; 530/817

(58) Field of Classification Search ........................ None
See application file for complete search history.

(56) References Cited

U.S. PATENT DOCUMENTS

| | | | |
|---|---|---|---|
| 4,506,083 A | 3/1985 | Kvita et al. ..................... 549/27 |
| 5,332,475 A | 7/1994 | Mechanic | |
| 5,410,016 A | 4/1995 | Hubbell et al. ................ 528/354 |
| 5,442,035 A * | 8/1995 | Corley et al. .................... 528/90 |
| 5,529,914 A | 6/1996 | Hubbell et al. ................ 435/182 |
| 5,573,934 A | 11/1996 | Hubbell et al. ................ 435/177 |
| 5,746,935 A * | 5/1998 | Corley et al. ............ 252/182.23 |
| 5,858,653 A | 1/1999 | Duran et al. ....................... 435/6 |
| 6,007,833 A | 12/1999 | Chudzik et al. ............... 424/425 |
| 6,217,894 B1 * | 4/2001 | Sawhney et al. .............. 424/426 |
| 6,258,870 B1 * | 7/2001 | Hubbell et al. ................. 522/26 |
| 6,410,044 B1 | 6/2002 | Chudzik et al. | |
| 6,669,994 B2 | 12/2003 | Swan et al. | |
| 7,427,415 B2 * | 9/2008 | Scharp et al. ................. 424/497 |
| 2002/0058318 A1 | 5/2002 | Hubbell et al. ............... 435/177 |
| 2003/0134032 A1 | 7/2003 | Chaouk et al. .............. 427/2.24 |

FOREIGN PATENT DOCUMENTS

WO   WO 87/00058   1/1987
WO   WO 02/100453   12/2002

OTHER PUBLICATIONS

Uludag et al., "Technology of mammalian cell encapsulation," *Adv. Drug Deliv. Rev.* 42, pp. 29-64 (2000).
Ashbrook et al., "Long Chain Fatty Acid Binding to Human Plasma Albumin," *J. Biol. Chem.*, vol. 250, No. 6, pp. 2333-2338 (1975).
Cruise et al., "In Vitro and In Vivo Performance of Porcine Islets Encapsulated in Interfacially Photopolymerized Poly(Ethylene Glycol) Diacrylate Membranes," *Cell Transplantation*, vol. 8, pp. 293-306 (1999).
Winter et al., "Improved synthesis and cationic polymerization of N-vinylmaleimide," *Macromol. Rapid Commun.* 15, pp. 867-872 (1994).
Schwanstecher, M. et al., "Photoaffinity labeling of the cerebral sulfonylurea receptor using a novel radioiodinated azidoglibenclamide analogue," J. Neurochem. 1994, 63:698-708.
Aguilar-Bryan, et al., "Photoaffinity labeling and partial purification of the beta cell sulfonylurea receptor using a novel, biologically active glyburide analog," J. Biol. Chem. 1990; 265:8218-8224.
Kramer, W. et al., "Direct photoaffinity labeling of the putative sulfonylurea receptor in rat beta-cell tumor membranes by [3H]-glibenclamide," FEBS Lett. 1988,229:355-359.

* cited by examiner

*Primary Examiner* — David Naff
(74) *Attorney, Agent, or Firm* — Kagan Binder, PLLC

(57) ABSTRACT

The present invention provides method and materials for forming a polymeric matrix having improved biocompatible properties. A polymerization accelerator is provided that includes an N-vinyl group and a biocompatible functional group. The polymerization accelerator is particularly useful for the polymerization of macromers, which can be used to form biocompatible polymeric coatings on the surface of biological materials, such as cells and tissue.

24 Claims, No Drawings

COMPOSITION CONTAINING BIOCOMPATIBLE POLYMERIZATION ACCELERATOR AND POLYMERIZABLE MATERIAL

FIELD OF THE INVENTION

The present invention relates to compounds and compositions that can be used to form polymeric matrices useful with biological systems. More particularly, the invention relates to compounds that can promote the formation of the polymeric matrices and provide biocompatible features to these matrices.

BACKGROUND

In recent years, the use of polymerizable oligomers to form polymeric matrices in situ for a wide variety of applications has greatly expanded. These reagents are generally polymeric materials that are capable of participating in additional polymerization reactions to form polymeric matrices. The use of reactive oligomers of this type to form polymeric matrices provides many advantages over standard matrix-forming technologies including polymerizations utilizing monomers. These oligomeric reagents, or macromers, can be polymerized rapidly, in an aqueous environment if desirable, to form polymeric matrices in the presence of living tissue and cells. The formation of polymeric matrices utilizing macromers of this type provide advantages such as reduced cytotoxicity, control over timing of matrix formation, speed of matrix formation, control over matrix characteristics, and the like. These reagents have found use in many applications, particularly in applications involving the formation of polymeric matrices in the presence of tissue or cells. These applications include the prevention of surgical adhesions, cell encapsulation, controlled drug delivery, tissue coatings, tissue adhesives, and the like.

For the prevention of surgical adhesions, a solution of polymerizable macromers is applied to a site of damaged tissue in a patient. Tissue damage generally occurs as the result of an invasive surgical procedure. During the course of the wound healing process, tissue "adhesions" can form between the damaged tissue and adjacent healthy tissue. The macromer solution is subsequently polymerized forming a solid polymeric matrix after application to the damaged and diseased tissue surface. This matrix acts as a barrier between healing tissue and surrounding tissues thereby preventing the formation of adhesions. If bioresorbable materials are used to form the matrix, the barrier will eventually disappear.

Cell encapsulation methods are generally aimed at surrounding a cell or group of cells with a synthetic material that provides protection from the processes of host immune rejection after the encapsulated cells have been transplanted into an individual. The synthetic material around the cells ideally allows the cells to remain viable and to function properly in order to provide therapeutic value to the host. In order to perform this function, the synthetic material that encapsulates the cells should be resistant to biodegradation and should be sufficiently permeable to allow for diffusion of cellular waste products, nutrients, and molecules involved in cellular responses. Preferably this synthetic material is not permeable to certain host molecules, such as immunoglobulins and complement factors that could contribute to the destruction of the foreign cells.

Advances in cell encapsulation technologies have been focused on improving the permeability, mechanical properties, immune protectivity, and biocompatibility of the encapsulating synthetic material. Various micro- and macro-encapsulation techniques, including microencapsulation by polyelectrolyte complexation, thermoreversible gelation, interfacial precipitation, interfacial polymerization, and flat sheet and hollow fiber-based macroencapsulation have been studied and are reviewed by Uludag et al. (*Adv. Drug Deliv. Rev.*; 42:29-64 (2000)).

One promising cell encapsulation process, interfacial polymerization, involves the formation of a layer of polymerized material, such as synthetic or natural polymerizable materials, on the surface of a biological substrate. Interfacial polymerization reagents and methods have been described in U.S. Pat. Nos. 5,410,016, and 5,529,914, and Applicant's U.S. Pat. Nos. 6,007,833 and 6,451,622, herein incorporated by reference in their entirety.

For controlled drug delivery, biologically active substances are delivered to desired tissue sites by incorporation into matrix-forming formulations. Tissue surfaces are coated with solutions of polymerizable macromers mixed with one or more biologically active substances and subsequently solidified by polymerization. Using this method, biologically active substances can be delivered to tissues over an extended period of time.

For tissue coatings, macromer solutions are applied to the surfaces of tissue and solidified in situ. The resulting polymeric matrices are useful for tissue healing, restenosis prevention, and the like.

For tissue adhesives, matrices formed by macromer polymerization can be used to adhere tissue surfaces in the body.

For all of these applications, the polymeric matrices themselves, the precursor macromer reagents, and the methods used to initiate and propagate polymerization should be biocompatible and have minimal cytotoxicity. In order to meet these requirements, rapid matrix formation is essential. To achieve rapid matrix formation, polymerization initiation and propagation efficiencies must be maximized. There are several methods of enhancing these efficiencies. One method is to provide the initiator in a polymeric form. Polymeric initiators enhance the initiation efficiency of polymerization reactions. Another method is to include a polymerization accelerator in the polymerization formulation.

Polymerization accelerators are low molecular weight monomers that enhance matrix formation when added to macromer formulations. Unfortunately, the inclusion of these accelerators may have a detrimental effect on the biocompatibility of the polymeric matrix.

The polymerization accelerators of the current invention address these fundamental problems associated with the formation of polymeric matrices in the presence of tissue. The inclusion of these new accelerators into macromer solutions enables the formation of biocompatible matrices when these formulations are polymerized into tissue-contacting matrices.

SUMMARY OF THE INVENTION

In one aspect, the invention provides compositions that include polymerizable material and a polymerization accelerator having a biocompatible functional group. Polymerization accelerators described herein are able to react with the polymerizable material to form a polymeric matrix having biocompatible properties. Therefore, the invention also provides biocompatible polymeric matrices formed by incorporation of the polymerization accelerator into the polymerizable material. In particular, the polymerization accelerators described herein can promote the formation of a polymeric matrix from a composition containing polymerizable polymers (macromers).

The compositions that include polymerizable material and a polymerization accelerator can also include a polymerization initiator. Particularly useful polymerization initiators include a photoinitiator group, such as a long-wave ultra violet- or visible light-activatable molecule. The composition can also include a macromer, as indicated, wherein preferred macromers are water-soluble macromers. The compositions can also include an acceptor or reductant.

The polymerization accelerator can include any of the following biocompatible functional groups: phosphonate ($PO_3^-$), sulfonate ($SO_3^-$), carboxylate ($COO^-$), hydroxyl (OH), albumin binding moieties, and phospholipid moieties. A preferred biocompatible functional group is a sulfonate group.

In another aspect, the polymerization accelerator includes an N-vinyl group. According to the invention, it has been discovered that, in particular, polymerization accelerators having an N-vinyl group are able to promote formation of a polymeric matrix from a composition that includes macromers. One group of polymerization accelerators described herein has an N-vinyl group and a carbonyl carbon. Preferred polymerization accelerators include an N-vinyl amide group. The N-vinyl group can be a part of a heterocyclic ring structure in some cases.

In another aspect, the invention provides polymerization accelerators that have a biocompatible functional group and an N-vinyl group. In particular polymerization accelerators having an N-vinyl amide and a sulfonate biocompatible functional group are described herein.

In another aspect, the invention provides a method for forming a biocompatible polymeric matrix. The method includes the steps of: (a) placing in contact with a surface at least the following materials: (i) a polymerization accelerator comprising a biocompatible functional group; (ii) a polymerizable compound; and (iii) a polymerization initiator; and (b) activating the polymerization initiator to promote formation of a biocompatible polymeric matrix on the surface. The method is particularly useful for coating biological surfaces, such as the surface or cells or groups of cells, for example tissue. The biocompatible functional group provided by the polymerization accelerator can improve the biocompatibility of the surface having the formed polymeric matrix.

More specifically, the polymerization accelerator of the invention can be used in a method for encapsulating cells. The method can include the steps of: (a) placing in contact with one or more cells at least the following materials: (i) a polymerization accelerator comprising a biocompatible functional group; (ii) a polymerizable compound; and (iii) a polymerization initiator; and (b) activating the polymerization initiator to promote formation of a biocompatible polymeric matrix on the one or more cells. Cells, such as endocrine cells from the pancreas, can be encapsulated with a matrix of polymeric material formed using the polymerization accelerator of the invention. The encapsulated cells can be introduced into a subject for therapeutic purposes.

In another aspect, the invention provides cellular material encapsulated with a biocompatible polymeric matrix formed by the polymerization of material that includes: (a) a polymerization accelerator having a biocompatible functional group; and (b) a macromer.

In another aspect, the invention provides a medical device coated with a polymeric matrix formed by the polymerization of material that includes: (a) polymeric material and (b) polymerization accelerator having a biocompatible functional group.

DETAILED DESCRIPTION

All publications and patents mentioned herein are hereby incorporated by reference. The publications and patents disclosed herein are provided solely for their disclosure.

The terminology used herein is not intended to limit the scope of the invention. Throughout the text, including the appended claims, the singular forms "a," "an," and "the" include plural reference unless the context clearly dictates otherwise. Thus, for example, a reference to "a cell" is a reference to one or more cells and includes equivalents thereof known to those skilled in the art. In this invention, certain terms are used frequently, the meanings of which are provided herein. Unless defined otherwise, terms used herein have the same meaning as commonly understood to one of ordinary skill in the art in this field of technology. Some terms may also be explained in greater detail later in the specification.

As used herein, an "initiator" for a polymerization reaction refers to a compound that can start a polymerization reaction, typically by providing a free radical species. The free radical species can be generated directly by the initiator compound, or can be abstracted from a compound that facilitates initiation of polymerization, for example, an "initiation facilitator", such as a tertiary amine. Polymeric initiators can enhance the initiation efficiency of polymerization reactions.

As used herein, an "accelerator" for a polymerization reaction refers to a compound that can assist the polymerization of polymerizable material following initiation of the reaction. Generally, an accelerator will promote completion of the polymerization reaction and/or increase the rate that the polymerizable material becomes incorporated into a polymerized product. Accelerators of the invention can be incorporated into the polymerized product and provide the product with (an) improved biocompatible feature(s). Suitable accelerators are generally lower molecular weight monomeric-type compounds that enhance matrix formation when added to and polymerized with a macromer-containing composition. Since the accelerator of the invention can be incorporated into a polymeric matrix it can sometimes be referred to as, for example, a "comonomer" or a similar term that denotes its role as a structural member of the polymeric matrix. However, as clearly set forth in the invention, the accelerator includes a biocompatible functional group and is able to promote the polymerization of a macromer solution to a polymeric matrix.

As used herein, "polymerizable material" refers to compounds having one or more polymerizable groups. Polymerizable groups are portions of polymerizable compounds that are able to propagate free radical polymerization, such as carbon-carbon double bonds. Suitable polymerizable material includes polymerizable monomers and polymerizable polymers.

Polymerizable polymers are herein referred to as "macromers". Macromers include one or more polymerizable groups. A polymeric matrix can be formed by the polymerization of a macromer-containing composition. Use of macromer-containing compositions can be advantageous for polymerization reactions in the presence of living biological material as it can provide, for example, compositions with increased viscosity and compositions that have low concentrations of small molecular weight compounds, such as monomers.

As used herein, "biological surfaces" broadly refers to the surface of any sort of biological material, such as, for example, the surface of cells, or the surface of a group of cells, or the surface of a tissue. "Tissue" refers to a biological mass that includes groups of similar cells, and also typically includes extracellular material that is associated with the cells. A "cell" refers to an individual membrane-bound biological unit that can be present as part of a tissue or organ, or can function independently as a microorganism.

The current invention provides methods and reagents for the acceleration of polymerization reactions useful for, for example, the encapsulation or coating of biological materials, including tissue and cells. In particular, the invention describes polymerization accelerators that have a biocompatible functional group useful for encapsulation or coating methods. In the presence of polymerizable material, the polymerization accelerators are able to promote the formation of, and be incorporated into, a polymeric matrix. Upon incorporation, the accelerator confers improved biocompatible properties to the matrix. The accelerators of the invention are particularly suitable for promoting the polymerization of macromers. In preferred embodiments the accelerators include N-vinyl groups.

The polymerization accelerator promotes the rapid polymerization of macromers on a surface, such as the surface of tissue or cells. This increased rate of polymerization can reduce the time needed for the encapsulation process to take place. This is beneficial as it can minimize the amount of time the cells are manipulated ex vivo, and thereby potentially improve the overall viability of the encapsulated cells. In addition, the increased rate of polymerization also minimizes the time the cells are in contact with any compounds present in the polymerization composition that can potentially have an adverse affect on the biological material. After polymerization, when the polymerization accelerator has been incorporated into the polymeric matrix, the biocompatibility of the polymerized matrix may be improved.

Improving the biocompatibility of the polymeric matrix formed using a composition containing the biocompatible polymerization accelerator is particularly advantageous in cell encapsulation processes. The polymeric matrix surrounding the encapsulated cells ideally provides benefits such as reduced immune rejection of the encapsulated cells, a reduction in the fibrotic growth surrounding the transplanted encapsulated cells, a reduction in hemo-incompatibility, and a reduction of the biodegradation of the polymeric matrix that encapsulates the cells.

In one embodiment, the invention provides a composition that includes a polymerization accelerator that has a biocompatible functional group and a polymerizable material. Under conditions that initiate a polymerization reaction, the polymerization accelerator can promote the polymerization of the polymerizable material and become associated with the polymerized product referred to as the polymeric matrix. The polymeric matrix acquires or improves its biocompatible properties due to the association with the polymerization accelerator.

Generally, a surface having (improved) biocompatible properties will more closely resemble a host surface as compared to a foreign surface. A substrate such as a tissue having a surface coated with the biocompatible polymeric matrix, as described herein, will be less likely subject to undesirable effects when introduced into a host. A substrate coated using the polymerization accelerator described herein can benefit from, for example, a reduced immune response against the surface, a reduction in fibrotic growth on the surface, a reduction in hemo-incompatibility, and a reduction in the biodegradation of the polymeric matrix.

Improved biocompatibility can be conferred by a biocompatible functional group, such as a negatively charged group. Examples of suitable negatively charged groups include sulphonate, phosphonate, and carboxylate groups. Hydroxyl groups can also provide biocompatibility. Other biocompatible functional groups can be provided by phospholipids, for example, phosphoryl choline, and albumin binding moieties, for example, long-chain fatty acids such as oleate, stearate, linoleate, and palmitate (Ashbrook et al., *J. Biol. Chem;* 250: 2333-2338 (1975). In some cases the biocompatible polymeric matrix can be prepared by using polymerization accelerators having different functional groups. In this aspect, the polymeric matrix can have more than one biocompatible feature that is provided by a combination of different accelerators.

The accelerator is used at a concentration in the polymerizable composition that is sufficient to provide the polymeric matrix with a desired degree of biocompatibility. For example, the polymeric matrix has an amount of pendent biocompatible groups allowing for improved biocompatibility. The accelerator is also used at a concentration that is sufficient to promote polymerization of the polymerizable material in the composition following initiation of the reaction. As described herein, amounts of the accelerator, the polymerizable material, and other reagents that can be used in a polymerization process are provided by weight percentage (wt %) of the total composition, unless otherwise indicated. It is also understood that due to minor variations associated with methods used to measure reagents, the scope of the invention includes the values provided herein, values that are approximate to these values, and ranges associated with these values.

The accelerator, in an amount of 0.05 wt % or greater, can be sufficient to promote the formation of a polymeric matrix from compositions that include macromers. A preferred range of accelerator in the composition is from about 0.05 wt % to about 1.0 wt %. Therefore, in a preferred embodiment, the composition includes a polymerizable material and a polymerization accelerator that has a biocompatible functional group, the accelerator being present at a concentration of 0.05 wt % or greater, and more preferably in the range of 0.05 wt % to 1.0 wt %, and most preferably in the range of 0.1 wt % to 0.5 wt %.

The polymerizable material is present in the polymerizable composition at a concentration sufficient to form a polymeric matrix. Generally, the polymerizable material is present at a concentration of about 0.5 wt % or greater. In some embodiments, for example, the polymerizable material includes a macromer that is present at a concentration in the range of about 0.5 wt % to about 50 wt %. More preferably the macromer concentration is in the range of about 1 wt % to about 30 wt %.

Testing for the incorporation of a polymerization accelerator comprising a biocompatible functional group into a polymeric matrix can be done using, for example, a Fourier Transform-Infra Red (FT-IR) spectrometer having Attenuated Total Reflectance (ATR). A suitable spectrometer for carrying out this analysis is, for example, the 560 Magna FT-IR spectrometer (Nicolet Instrument Corp., Madison, Wis.) equipped with a SensIR multi-bounce diamond ATR accessory.

Suitable accelerators include a biocompatible functional group and are able to promote the polymerization of macromers after polymerization is initiated. It has been discovered that the polymerization accelerators provided by the invention are able promote the polymerization of a composition containing macromers, in particular.

According to the invention, polymerization accelerators having an N-vinyl group, for example, a group wherein a carbon atom of an ethylenically unsaturated group is bound to a nitrogen atom, are able to promote the polymerization of macromers into a polymeric matrix following polymerization initiation. Suitable N-vinyl groups are represented by the following formulas: $CH_2=CH-NH-$ and $CH_2=CH-N-$. Therefore, in some embodiments, the invention provides a composition that includes (a) a polymerization accelerator having (i) a biocompatible functional group and (ii) an N-vinyl group and, (b) a polymerizable material.

The nitrogen of the N-vinyl group of the accelerator can be a part of a single or fused organic ring system. The N-vinyl nitrogen can also be a part of a compound having a straight or branched chain. The straight or branched chain can also be attached to any heterocyclic, alicyclic, bicyclic, tricyclic, polycyclic aromatic ring or any heterocyclic, alicyclic, or aromatic fused ring system. An organic ring, either singly or a part of a fused ring structure, can contain at least 4, and up to 10 atoms having any combination of C, N, O or S atoms.

Suitable polymerization accelerators wherein the N-vinyl nitrogen is part of a ring structure are represented by Formula I and Formula II:

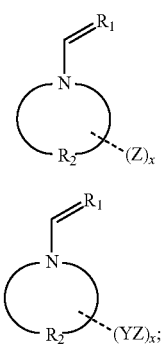

(Formula I)

(Formula II)

wherein $R_1$ is $CH_2$; $R_2$ include atoms which form one or more ring structures with the N-vinyl nitrogen, said ring structures having one or more of C, N, O, S, or combinations thereof, wherein any of the ring atoms can be linked to additional atoms or chemical groups; Z includes a biocompatible group, for example, $PO_3^-$, $SO_3^-$, $COO^-$, OH, albumin binding moieties, and phospholipid moieties; X is at least one or greater; and, for Formula II, Y is a spacer portion separating the ring portion from Z and can be a carbon-containing chain, for example, an alkyl or alkoxy chain.

Suitable ring structures include heterocyclic rings having a single nitrogen, wherein the single nitrogen is the N-vinyl nitrogen, for example, pyrrolidine- and piperidine-based ring structures; and pyrrole-, isopyrrole-, and pyridine-based ring structures and hydrogenated derivatives thereof. Other contemplated heterocyclic rings containing a single nitrogen include oxazole-, thiazole-, oxazine-, oxathiazine-based heterocyclic ring structures and hydrogenated derivatives thereof. Contemplated heterocyclic rings having two nitrogens include, for example, piperazine-based ring structures; imidazole-, pyrazole-, pyrazine-, pyrimidine, pyridazine-based ring structures, and hydrogenated derivatives thereof. The nitrogen-containing ring structure can also be a part of a fused ring structure having two or more fused rings, for example, indole-, indazole-, indoxazine-, quinoline-, cinnoline-based ring systems, and hydrogenated derivatives thereof; and aza-bicyclo alkane-based ring systems.

In other embodiments, the polymerization accelerator of the invention includes N-vinyl compounds wherein the N-vinyl nitrogen is a part of a straight or branched chain structure represented by Formula III:

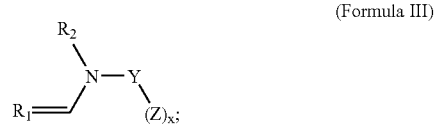

(Formula III)

wherein $R_1$ is $CH_2$; $R_2$ is H, a carbon-containing chain, a ring system, or combinations of a chain and ring system which can include one or more of C, N, O, and S, or any combination thereof, and wherein any of these atoms can be linked to additional atoms or chemical groups; Y is a covalent bond or a spacer coupling the N-vinyl nitrogen to Z; Z includes a biocompatible group, for example, $PO_3^-$, $SO_3^-$, $COO^-$, OH, albumin binding moieties, and phospholipid moieties; and X is at least one.

In some embodiments, the invention provides (a) a polymerization accelerator having (i) a biocompatible functional group, (ii) an N-vinyl group and, (iii) a carbonyl carbon. In yet other embodiments, more specifically, the nitrogen of the N-vinyl group shares a bond with the carbon of the carbonyl carbon, which is herein referred to as an "N-vinyl amide" group and represented by Formula IV:

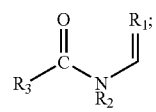

(Formula IV)

wherein $R_1$ is $CH_2$; $R_2$ is a group that allows the N-vinyl nitrogen to be a secondary or tertiary amide, for example, $R_2$ is H or an alkyl group; and $R_3$ is H, a carbon-containing chain, a ring system, or combinations or a chain and ring system. A biocompatible functional group can be coupled to $R_3$, or in some cases, $R_2$.

In other embodiments, the invention provides a polymerization accelerator having a biocompatible functional group and an N-vinyl amide, wherein the N-vinyl nitrogen is part of a ring, and which can be represented by compounds of Formula V:

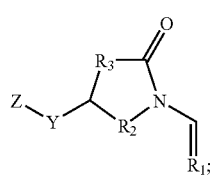

(Formula V)

wherein $R_1$ is $CH_2$; $R_2$ is a covalent bond, 1-4 carbon, oxygen, nitrogen, or sulphur, or combinations thereof; $R_3$ is a covalent bond, 1-4 carbon, nitrogen, or combinations thereof, with the provision that $R_2$ and $R_3$ are not both covalent bonds; optionally $R_2$ includes a carbonyl carbon; Z is a functional group that confers biocompatibility and is selected from $PO_3^-$, $SO_3^-$, $COO^-$, OH, albumin binding moieties, phospholipid moieties, and the like; Y is a covalent bond ($Y_0$,) or a spacer ($Y_1$) between the ring structure and group Z, wherein $Y_1$ is 1-4 carbon alkyl, 1-4 carbon alkoxy, oxygen, nitrogen, or combinations thereof. Preferred spacers include, for example, polyethylene oxide or polypropylene oxide. In some embodiments, atoms of $R_2$ and $R_3$ can be bonded to form an aza-bicyclic ring compound. Preferred ring structures are ones that have at least one nitrogen and that also include at least one carbonyl carbon, for example, lactam-based rings, such as pyrrolidine; imide-based rings, such as succinimide; and aza-bicyclo alkanone rings, such as aza-bicycloheptanone.

Examples of N-vinyl lactam rings suitable for a core ring structure in the polymerization accelerator include N-vinyl capryllactam (1-vinyl-azonan-2-one), N-vinyl enatholactam (1-vinyl-azocan-2-one), N-vinyl caprolactam (1-vinyl-azepan-2-one), N-vinyl valerolactam (1-vinyl-piperidin-2-one), and N-vinyl butyrolactam (1-vinyl-pyrrolidin-2-one). Examples of cyclic N-vinyl amides suitable for a core ring structure in the polymerization accelerator include N-vinyl succinimide (1-vinyl-pyrrolidine-2,5-dione), N-vinyl glutarimide (1-vinyl-piperidine-2,6-dione), N-vinyl malemide (1-vinyl-pyrrole-2,5-dione), and N-vinyl phthalimide (2-vinyl-isoindole-1,3-dione). Examples of aza-bicyclo alkanone rings suitable for a core ring structure in the accelerator molecule include, for example, 2-vinyl-2-aza-bicyclo[2.2.1]heptan-3-one and 6-vinyl-6-aza-bicyclo[3.2.1]octan-7-one. According to the structure of the N-vinyl lactam, N-vinyl amide, and N-vinyl aza-bicyclo alkanone rings, one or more biocompatible functional groups can be attached to any non-carbonyl carbon on the ring structure(s), optionally spaced from the ring structure(s) by a spacer.

In other embodiments, the invention provides a polymerization accelerator having a biocompatible functional group and an N-vinyl amide wherein the N-vinyl amide is part of a chain or branched structure that can be represented by compounds of Formula VI:

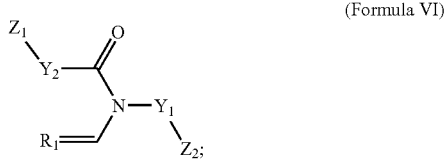

(Formula VI)

wherein $R_1$ is $CH_2$; $Z_1$ and $Z_2$ are functional groups that confer biocompatibility, independently selected from $PO_3^-$, $SO_3^-$, $COO^-$, OH, albumin binding moieties, phospholipid moieties, and the like; optionally, one of $Z_1$ or $Z_2$ is H; $Y_1$ is a spacer of 1-4 carbon alkyl; 1-4 carbon alkoxy; 1-4 carbon; secondary amine; 4-9 carbon heterocyclic, fused, bicyclic, or aliphatic rings; and $Y_2$ is a covalent bond, $Y_1$, or oxygen. Preferred 1-4 carbon alkoxy groups include, for example, polyethylene oxide or polypropylene oxide.

Other useful polymerization accelerators having a biocompatible group and an N-vinyl nitrogen bonded to a carbonyl carbon include linear and cyclic compounds having an N-vinyl urea group such as vinyl urea and 1-vinyl imidizolidone, respectively, linear and cyclic compounds having an N-vinyl urethane group, for example, a vinyl-carbamic acid methyl ester and N-vinyl oxazolidinone.

In other embodiments, the invention provides compositions that include (a) a polymerization accelerator according to Formula I, II, III, IV, V, or VI; and (b) a polymerizable material. The polymerizable material is preferably a macromer.

In other embodiments, the invention provides a method for forming a biocompatible polymeric matrix comprising the steps of (a) providing a polymerization initiator; (b) providing a polymerizable compound; (c) providing a polymerization accelerator Formula I, II, III, IV, V, or VI; and (d) activating the polymerization initiator thereby promoting formation of a biocompatible polymeric matrix. The polymerizable material is preferably a macromer.

In preferred embodiments the polymerization accelerator includes a biocompatible group that includes a sulfonate group referred to herein as "sulfonated N-vinyl accelerators". Therefore, more specifically, the invention provides a composition that includes (a) a polymerization accelerator having (i) a sulfonate group, (ii) an N-vinyl group, and (iii) a carbonyl carbon; and (b) a polymerizable material.

Useful sulfonated N-vinyl accelerators include compounds having an N-vinyl portion coupled to an amide (C=C—N—(C=O)—) and one or more sulfonate groups ($SO_3^-$). Sulfonated N-vinyl amide accelerators can be chemically referred to as N-vinyl amide sulfonates. The sulfonate groups on the sulfonated N-vinyl amide accelerator can be provided in the form of any suitable derivative, such as a sulfonic acid group or a sulfonate salt. In addition, optionally, the sulfonate group can be spaced from the N-vinyl portion with any suitable spacer, such as an alkyl or alkoxy spacer.

Compounds included in this group include sulfonated N-vinyl amides such as sulfonated N-vinyl carboxamides and sulfonated N-vinyl lactams. Examples of sulfonated N-vinyl lactams include compounds having hetero ring structures containing one nitrogen and, for example, from 4 to 10 carbon atoms. One or more sulfonate groups can be attached to any non-carbonyl carbon of the lactam ring structure. The sulfonate group can be attached via a linker, such as an alkyl or alkoxy linking portion. Examples include sulfonated N-vinyl capryllactam (1-vinyl-azonan-2-one), sulfonated N-vinyl enatholactam (1-vinyl-azocan-2-one), sulfonated N-vinyl caprolactam (1-vinyl-azepan-2-one), sulfonated N-vinyl valerolactam (1-vinyl-piperidin-2-one), and sulfonated N-vinyl butyrolactam (1-vinyl-pyrrolidin-2-one), and the like.

Examples of sulfonated N-vinyl carboxamides include linear molecules having one sulfonate group or branched molecules having more than one sulfonate group. Examples of linear sulfonated N-vinyl carboxamides include vinylcarbamoyl-methanesulfonate, 2-vinylcarbamoyl-ethane-sulfonate, 3-vinylcarbamoyl-propane-1-sulfonate, 4-vinyl-carbamoyl-butane-1-sulfonate, 5-vinylcarbamoyl-pentane-1-sulfonate, 6-vinylcarbamoyl-hexane-1-sulfonate, 7-vinylcarbamoyl-heptane-1-sulfonate, and the like.

Another group of suitable sulfonated N-vinyl accelerators includes compounds wherein the N-vinyl nitrogen is bonded to two carbonyl groups. Compounds in this group include sulfonated N-vinyl imides, in particular, sulfonated cyclic N-vinyl imides. Examples of sulfonated cyclic N-vinyl imides include sulfonated N-vinyl succinimide (sulfonated 1-vinyl-pyrrolidine-2,5-dione), sulfonated N-vinyl glutarimide (sulfonated 1-vinyl-piperidine-2,6-dione), and sulfonated N-vinyl phthalimide (sulfonate 2-vinyl-isoindole-1,3-dione) and the like.

In some embodiments, the sulfonated N-vinyl accelerator can be used at a concentration suitable to promote the formation of a matrix of polymerized material following activation of the initiator. Preferably, the sulfonated N-vinyl accelerator is present in the polymerizable composition in a range from 0.05-1.00 wt % and more preferably from 0.1-0.5 wt %.

As discussed herein, it has been found that accelerators having N-vinyl groups are able to promote the polymerization of a composition containing macromers. The accelerator activity of the polymerization accelerator can be determined by assessing the rate of matrix formation using a polymerizable composition containing a macromer, an initiator, and an N-vinyl accelerator having a biocompatible functional group. The activity of the N-vinyl accelerator can be determined by comparing the rates of polymerization of macromer-containing compositions with and without the N-vinyl accelerator.

Suitable macromers for assessing matrix-forming ability include polymerizable hyaluronic acid and similar polymerizable polymers. Compositions including the polymerization accelerator can be applied to a substrate and treated to initiate the polymerization of the macromer material. Following the treatment, the treated composition on the substrate can be analyzed for formation of a gelled matrix of polymerized macromer. Evaluations can include physical assessment of the firmness of the gel and elastomeric properties of the gel. Typically, compounds that do not display accelerator activity do not allow for the formation of a gel and the composition remains in a liquid state.

The polymerizable composition having the polymerization accelerator can be used to form a polymerized product for any desired use. Useful applications include forming matrices of polymerized material on biological surfaces for therapeutic purposes. The polymerizable material can be any sort of compound, including monomers and polymers having one or more polymerizable groups. Polymerizable groups are portions of the polymerizable compounds that are able to propagate free radical polymerization, such as carbon-carbon double bonds. Preferred polymerizable groups are found in polymerizable compounds having vinyl or acrylate groups. More specifically, polymerizable portions include acrylate groups, methacrylate groups, ethacrylate groups, 2-phenyl acrylate groups, acrylamide groups, methacrylamide groups, itaconate groups, and styrene groups. Preferred materials for the encapsulation of cellular material are biocompatible polymerizable polymers (macromers). Such macromers can be straight chain or branched polymers or copolymers, or graft copolymers. Synthetic polymeric macromers, polysaccharide macromers, and protein macromers suitable for use with the accelerator of the current invention are described in U.S. Pat. No. 5,573,934 (Hubbell et al.).

Preferred macromers include, but are not limited to, polymerizable poly(vinylpyrrolidone) (PVP), poly(ethylene glycol) (PEG), poly(ethylene oxide) (PEO) poly(ethyloxazoline), poly(propyleneoxide), polyacrylamide (PAA), poly (vinyl alcohol) (PVA), copolymers thereof, and the like. These types of macromers are typically soluble in water and are more stable in vivo as compared to biodegradable polymers. In particular, PEG and PAA are preferred macromers.

In some cases it may be desirable to use naturally occurring or synthetic macromers as the polymerizable material. Suitable macromers include naturally occurring polymers such as polysaccharides, examples of which include, but are not limited to, hyaluronic acid (HA), starch, dextran, heparin, and chitosan; and proteins (and other polyamino acids), examples of which include, but are not limited to, gelatin, collagen, fibronectin, laminin, albumin, and active peptides thereof. In order to make these naturally occurring or synthetic macromers polymerizable, polymerizable groups can be incorporated into a polymer using standard thermochemical reactions. For example, polymerizable groups can be added to collagen via reaction of amine containing lysine residues with acryloyl chloride. These reactions result in collagen that contains polymerizable moieties. Similarly, when synthesizing a macromer, monomers containing reactive groups can be incorporated into the synthetic scheme. For example, hydroxyethylmethacrylate (HEMA) or aminopropylmethacrylamide (APMA) can be copolymerized with N-vinylpyrrolidone or acrylamide yielding a water-soluble polymer with pendent hydroxyl or amine groups. These pendent groups can subsequently be reacted with acryloyl chloride or glycidyl acrylate to form water-soluble polymers with pendent polymerizable groups. Suitable synthetic polymers include hydrophilic monomers containing degradable segments as described in U.S. Pat. No. 5,410,016 supra.

The polymerizable composition also includes an initiator system capable of initiating free radical polymerization, either directly or indirectly. Indirect methods typically include the transfer of energy from the activated initiator to an acceptor or reductant, a chemical species that can form a free radical and cause free radical polymerization of the polymerizable material.

The initiator system can be utilized by itself, for example, not being coupled to a compound having a different functionality, or it can be coupled to a compound such as a polymer, for example, an initiator polymer. An initiator polymer can include one or more initiator portions or initiator groups. The initiator system, upon activation, directly or indirectly promotes the free radical polymerization of the polymerizable material. In some cases an initiator is used that can be localized at the surface of the biological material, for example, through an affinity interaction or the like. These events lead to the formation of a layer of polymeric matrix on a biological surface.

The initiator system can include light-activated photoinitiator groups, thermally activated initiator groups, chemically activated initiator groups, or combinations thereof. Suitable thermally activated initiator groups include 4,4' azobis(4-cyanopentanoic) acid and 2,2-azobis[2-(2-imidazolin-2-yl) propane] dihydrochloride or other thermally activated initiators. Chemically activated initiation is often referred to as redox initiation, redox catalysis, or redox activation. In general, combinations of organic and inorganic oxidizers, and organic and inorganic reducing agents are used to generate radicals for polymerization. A description of redox initiation can be found in *Principles of Polymerization*, $2^{nd}$ Edition, Odian G., John Wiley and Sons, pgs 201-204, (1981). Redox initiators that are not damaging to biological systems are preferably used. Photoinitiator groups and thermally activated initiator groups that utilize energy that is not damaging to biological systems are preferably used.

Photoinitiation can occur by various mechanisms, including Norrish type I reactions, intra- or intermolecular hydrogen abstraction reactions, and photosensitization reactions utilizing photoreducible or photo-oxidizable dyes. The latter two types of reactions are commonly used with an energy transfer acceptor or a reductant, which can be, for example, a tertiary amine. Such tertiary amines can be incorporated into the polymeric backbone of the macromer. The initiator system includes one or more initiator groups that allow for intra- or intermolecular hydrogen abstraction reactions or photosensitization reactions utilizing photoreducible or photo-oxidizable dyes when activated. Useful energy transfer acceptors or reductants for use with these types of initiators include, but are not limited to, tertiary amines such as triethanolamine, triethylamine, N-methyl diethanolamine, N,N-dimethyl benzylamine, tetramethyl ethylenediamine; secondary amines such as dibenzyl amine, N-benzyl ethanolamine, N-isopropyl benzylamine; and primary amines such as ethanolamine, lysine, and ornithine.

Photoinitiator groups having an absorbance of 350 nm and greater are used. More preferably, photoinitiator groups having an absorbance of 500 nm and greater are used. Suitable photoinitiator groups include light-activated initiator groups, such as long-wave ultra violet (LWUV) light-activatable molecules and visible light activatable molecules. Suitable long-wave ultra violet (LWUV) light-activatable molecules include, but are not limited to, ((9-oxo-2-thioxanthanyl)-oxy) acetic acid, 2-hydroxy thioxanthone, and vinyloxymethylbenzoin methyl ether. Suitable visible light activatable photoinitiator groups include, but are not limited to, acridine orange, camphorquinone, ethyl eosin, eosin Y, erythrosine, fluorescein, methylene green, methylene blue, phloxime, riboflavin, rose bengal, thionine, and xanthine dyes.

According to the invention, the product of the polymerization of the composition containing the polymerization accelerator and polymerizable material provides a matrix of polymerized material bearing biocompatible functional groups. In one embodiment, the invention provides a matrix of polymerized material having sulfonate groups, the matrix being formed by the incorporation of the polymerization accelerator having sulfonate groups into the polymerized material.

This matrix of polymerized material can impart desirable properties to various coated surfaces. In particular, coated materials that are introduced into a portion of the body may have improved biocompatibility within the body. Such coated materials include coated, for example, encapsulated, cells or cellular material, and coated implantable medical devices. Improved biocompatibility refers to the ability of the coated material to be relatively free of unwanted effects associated with introduction of the coated material into the body, such as, for example, immune rejection, fibrotic overgrowth, hemoincompatibility, and biodegradation of the matrix.

In particular, the sulfonated N-vinyl accelerator can be used as a reagent for cell encapsulation and can provide the encapsulated cells with a biocompatible polymeric coating. The polymeric coating may improve biocompatibility by mimicking the negatively charged surface of a living cell without displaying antigenic determinants that provoke a host immune response. Such a reduction may be manifested in a reduction in the attachment or attraction of immune cells, such as macrophages or lymphocytes, or a reduction in the attachment of immune molecules, such as antibodies, to the surface of the encapsulated material.

In addition, cells that have been encapsulated with a matrix of polymeric material having a biocompatible functional group, for example, a sulfonate group, may also demonstrate improved hemocompatibility. Improved hemocompatibility refers to the ability of the coated material to be relatively free of effects associated with coagulation of blood components, such as the reduction in clotting time, fibrin assembly, thrombin activation, and platelet attachment and spreading. Therefore, the coating provided by the composition of the invention may reduce the likelihood that blood components will adversely affect the integrity and function of the coated material in the body. For example, coatings formed using compositions of the invention may reduce the amount of platelets and thrombus deposition on the surface of the coated material, for example on encapsulated cellular material.

Therefore, the capsule formed from the polymeric composition including the accelerator having the biocompatible group, for example, the sulfonated N-vinyl accelerator, may improve the function of the encapsulated and transplanted cells by reducing the likelihood of destruction or prevention of function by host components.

As previously indicated, the composition containing the biocompatible polymerization accelerator of the invention is typically used with macromers and, in some cases, a reductant/acceptor in a method to provide a coating to a biological surface. The reagents are particularly suitable for cell encapsulation processes.

Cells or tissue to be encapsulated can be obtained from an organism, for example, a human donor, or obtained from a cell culture, wherein the cells can be transformed or otherwise modified. Specific types of cells and tissue that can be encapsulated and used for the treatment of diseases are discussed below. Cells, or tissue in particular, can be subject to treatment prior to the encapsulation process. For example, tissue can be treated with enzymatic or other suitable reagents, such as trypsin, hyaluronidase, or collagenase to obtain individual cells or cell groups of a suitable size for the encapsulation process. Alternatively, tissue can be subject to mechanical processes in order to prepare suitable cellular starting material. Prior to encapsulation, cells can also be treated with drugs, prodrugs, hormones, or the like, or can be cultured to provide cells that display a desired expression pattern or have a certain morphological features. Technical references that provide detailed instructions for the preparation of cells or tissue and the treatment of prepared cells or tissue are available and can be found in, for example, in *Basic Cell Culture Protocols*, Pollard, J. W. and Walker, J. M., Ed. (1997).

Alternatively, cells or tissue suitable for encapsulation and intended for use with the biocompatible polymerization accelerator composition of the invention can be commercially obtained. For example, viable human liver preparations such as microsomes and hepatocytes, and viable human pancreatic preparations such as pancreatic islets, can be obtained from commercial sources such as CellzDirect, Inc. (Tucson, Ariz.).

With information available in technical literature, one can utilize the biocompatible polymerization accelerator composition in methods for coating a surface, and in particular, in the novel and inventive methods as described herein for encapsulating cells and tissue. For example, the teaching of Cruise, et al., *Cell Transplantation* 8:293 (1999), can provide a basis for the cell encapsulation methods using the biocompatible polymerization accelerator composition of the invention.

Cells or tissue suitable for the encapsulation process, prepared as indicated above or obtained from a commercial source, can be suspended in a suitable solution, such as a biocompatible buffered aqueous solution, such as Roswell Park Memorial Institute (RPMI) media. Other reagents can be added to this solution, such as animal serum; proteins such as albumin; oxidants; reductants; vitamins; minerals; growth factors; or other components that can have an impact on the viability and function of the cells or tissues.

The polymerization accelerator can be added to a solution containing polymerizable material before or after contacting the cells or tissue with the solution. The initiator can be brought into contact with the cells in an amount that is sufficient for formation of a matrix around the cells or tissue. Useful concentrations of the polymerization accelerator are from 0.05 to 1.00 wt % in the polymerizable composition. Optionally, a washing step can be performed. This washing step can be used, for example, to remove excess initiator or other material in contact with the cells. After the polymerization accelerator is brought in contact with the cells or tissue, the polymerizable material, such as macromers, can be brought in contact with the cells.

In another embodiment, the polymerization accelerator is brought into contact with the cells or tissue together with the polymerizable material. In yet another embodiment the polymerizable material is brought into contact with the cells prior to bringing the polymerization accelerator into contact with the cells.

The polymerizable material, for example, macromers, can be brought into contact with the cell or tissue in an amount that allows formation of a matrix of a desired thickness. A concentration of macromer in solution useful for cell encapsulation can be in the range of 5-50 wt %, and more preferably in the range of 10-30 wt %. In some embodiments, the polymerizable material can be placed in contact with the cells for a period of time prior to initiating the polymerization reaction.

Other reagents can be brought in contact with the cells or tissue during the encapsulation process. As previously mentioned, such reagents include acceptors or reductants, such as tertiary amines, for example, triethanolamine, that can form a free radical and cause free radical polymerization of the polymerizable material. Suitable acceptors or reductants are known in the art and are commercially available. These acceptors or reductants are typically used in indirect polymerization methods wherein the initiator group transfers energy to the acceptors or reductants to promote free radical polymerization of the polymerizable material. Reagents such as viscosity-enhancing reagents can also be used in the method of the invention. Viscosity-enhancing reagents can improve the process of polymerization. Suitable viscosity-enhancing reagents are known in the art and are commercially available. One of skill in the art can determine suitable amounts of any of these additional reagents for performing the encapsulation process.

After the reagents necessary to promote formation of a matrix are brought in contact with the surface to be coated, a source of energy, such as a thermal or electromagnetic energy sufficient to activate the initiator group, is applied to initiate polymerization of the polymerizable material. Long-wave ultra violet (LWUV) and visible wavelengths in range of 350 nm to 900 nm are preferred and can be supplied by lamps and laser light sources. Lamps or laser light sources that can provide these wavelengths of light are commercially available and can be obtained from, for example, EFOS Inc. (Mississauga, Ontario, Canada). A particularly suitable wavelength is about 520 nm. The time and temperature of the reaction are maintained to provide a desired coating. For example, the cells or tissue in contact with the initiator system, accelerator, and macromer can be treated with light for a period in the range of seconds to minutes. The encapsulated cells or tissue can then be subject to further treatment if desired. For example, it may be desirable to concentrate the encapsulated material, for example, by centrifugation, prior to introducing the encapsulated material into a subject.

As indicated, a number of technical references that provide detailed procedures for encapsulating cells are available. Therefore using the available information, one can perform surface coating of a material, more specifically, the encapsulation of cellular material and tissue using the biocompatible polymerization accelerator composition and reagents described herein or in other references.

The invention can also provide a method for reducing potential toxicity associated with providing a polymerizable composition to an animal. For example, the use of the polymerization accelerator having a biocompatible functional group can allow for the use of polymerizable compositions, particularly in situ, that present minimal or no toxicity risks to living materials and organisms. This can be due, at least in part, to the ability of the polymerization accelerators of the invention to drive the polymerization of the polymerizable material to completion, for example by accelerating the rate of polymerization, resulting in the consumption of potentially harmful starting materials, such as monomers. In addition, one or more sulfonate, phosphonate, carboxylate, hydroxyl, phospholipids, or albumin binding functional groups can increase the hydrophilic properties of the accelerator and improve solubility of the biocompatible polymerization accelerator composition in an aqueous medium.

According to the invention, a polymerizable composition containing the polymerization accelerator can be used to promote the formation of a matrix of polymerized material on a biological surface. Polymerization using the biocompatible polymerization accelerator composition can be performed in vivo by applying a composition containing the polymerization accelerator and a polymerizable material, either together or separately, to a subject in either an invasive or in a noninvasive procedure. Other particularly useful applications involve the ex vivo encapsulation of cells or tissue. In this application cells or tissue can be obtained from a suitable source, encapsulated with a matrix of polymeric material using a composition including the polymerization accelerator described herein, and then introduced into a subject in need of the encapsulated cells or tissue. In some cases, after receiving the transplanted encapsulated cells, the subject can be administered a pharmaceutical agent that can penetrate the matrix that encapsulates the cells and can provoke a cellular response which is of therapeutic value to the subject. This type of ex vivo encapsulation and transplantation procedure is advantageous as it can provide a matrix coating affording the transplanted cells protection from host immune rejection while allowing the encapsulated cells to provide a therapeutic value to the host.

In one aspect of the invention, a composition containing the polymerization accelerator is used to encapsulate cells or tissue from glands and organs of the endocrine system, which include cells from the pituitary gland; cells from the adrenal gland; cells from the thyroid/parathyroid glands; cells from the pancreatic islets, such as beta cells, alpha cells, delta cells, and pancreatic polypeptide (PP) cells; cells from the liver; and cells from reproductive glands such as the testis and ovary. Endocrine cells can be removed from a donor individual and encapsulated with polymeric material using the biocompatible polymerization accelerator composition as described herein.

Encapsulated endocrine cells can be transplanted to an individual having any of the following conditions or needs: a pituitary disorder and in need of growth hormone (GH), adrenocorticotropic hormone (ACTH), follicle stimulating hormone (FSH), leutinizing hormone (LH), thyroid stimulating hormone (TSH), oxytocin, or antidiuretic hormone (ADH); an adrenal disorder and in need of mineralcorticoids (for example, aldosterone) glucocorticoids (for example, cortisol), androgenic steroids, or catecholamines such as epinephrine or norepinephrine; a thyroid or parathyroid disorder and in need of thyroxin, calcitonin, or parathyroid hormone (PTH); a pancreatic disorder such as diabetes and in need of insulin, glucagon, somatostatin, or pancreatic polypeptide; a liver disorder and in need of bile or plasma proteins, including clotting factors; a reproductive gland disorder and in need of male hormones such as testosterone or female hormones such as estrogen.

Other types of cells that can be encapsulated include immature and mature cells from the cardiovascular, respiratory, renal, nervous, muscular, and skeletal systems. In some aspects cells that have been transformed or genetically modified can be encapsulated and transplanted into a host. For example, cells that have been transformed or modified to produce a therapeutically useful compound, such as a peptide hormone or an enzyme can be encapsulated and introduced into an individual.

The invention also specifically provides interfacial polymerization compounds, compositions, and methods for the treatment of diabetes. In particular, the invention provides for compositions containing the polymerization accelerator that are useful for providing formation of a biocompatible polymeric layer around insulin producing cells and islets.

As stated above, in some instances, a pharmaceutical agent can be administered to the subject after transplantation of the encapsulated cells. The pharmaceutical agent can provoke a therapeutically useful cellular response from the encapsulated cells if needed. Other drugs that can stimulate insulin production and that can be coadministered with the transplanted encapsulated insulin producing cells include metformin, acarbose, and troglitazone. Other useful drugs that can be administered to subjects having encapsulated cells include antithrombogenic, anti-inflammatory, antimicrobial, antiproliferative, and anticancer compounds, as well as growth factors, morphogenic proteins, and the like.

In another aspect, a composition containing the accelerator and a polymerizable material can also be used in in vivo applications to provide artificial barriers, for example, barriers to prevent tissue adhesion following surgery. For this application, the polymerization accelerator along with polymerizable material is applied to the surface of the tissue. The composition is then illuminated to initiate polymerization and a barrier matrix is formed. The polymeric matrix prevents other tissue from adhering to the coated tissue. In some procedures a polymeric matrix can be formed on the surface of a blood vessel to prevent blood factors or cells, such as platelets, from interacting with or adhering to the blood vessel wall. Both degradable and non-degradable macromer systems can be used for this purpose.

Compositions containing the polymerization accelerator of the invention can also be utilized for other medically useful purposes. For example, a composition containing the polymerization accelerator can be a component used for forming adhesives for tissue and other surfaces. If a temporary adhesive is desired, the polymerizable material can include a degradable material, for example, biodegradable macromers.

Compositions containing the polymerization accelerator can be used for the formation of barriers on surfaces. An example of such an application is a barrier for the prevention of tissue adhesion following surgery. For this application, a composition containing the polymerization accelerator and polymerizable material can be applied to the surface of damaged tissue. The composition can then be activated on the surface to polymerize the polymerizable material. The polymeric matrix formed by this polymerization can prevent other tissue from adhering to the damaged tissue. Both degradable and/or non-degradable macromers can be used in this barrier formation method.

The polymerization accelerator can also be used to provide coatings to a surface of a medical device, preferably those devices that are useful in the course of implantation or use in vivo. In an embodiment, a composition comprising the polymerization accelerator and polymerizable material are applied to a surface of an implantable medical device. The composition can be activated on the surface to polymerize the polymerizable material to form a biocompatible polymeric matrix. The structure and composition of the underlying device can be of any suitable, and medically acceptable, design and can be made of any suitable material that is compatible with the coating itself. Optionally, a coating of the biocompatible polymeric matrix on the surface of the medical device can include one or more bioactive agents.

Suitable implantable medical devices can be fabricated from a variety of biomaterials. Preferred biomaterials include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, styrene, vinyl chloride, vinyl acetate, and vinyl pyrrolidone. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetheretherketone.

Certain natural materials are also suitable biomaterials, including human tissue such as bone, cartilage, skin and teeth; and other organic materials such as wood, cellulose, compressed carbon, and rubber. Other suitable biomaterials include metals and ceramics. The metals include, but are not limited to, titanium, stainless steel, and cobalt chromium. A second class of metals includes the noble metals such as gold, silver, copper, and platinum. Alloys of metals, such as nitinol, may be suitable for biomaterials as well. The ceramics include, but are not limited to, silicon nitride, silicon carbide, zirconia, and alumina, as well as glass, silica, and sapphire. Combinations of ceramics and metals would be another class of biomaterials. Another class of biomaterials is fibrous or porous in nature. The surface of such biomaterials can be pretreated, for example, with a Parylene coating composition, in order to alter the surface properties of the biomaterial.

Biomaterials can be used to fabricate a variety of implantable devices. General classes of suitable implantable devices include, but are not limited to, vascular devices such as grafts, stents, catheters, valves, artificial hearts, and heart assist devices; orthopedic devices such as joint implants, fracture repair devices, and artificial tendons; dental devices such as dental implants and fracture repair devices; drug delivery devices; ophthalmic devices and glaucoma drain shunts; urological devices such as penile, sphincter, urethral, bladder, and renal devices; and other catheters, synthetic prostheses such as breast prostheses and artificial organs. Other suitable biomedical devices include dialysis tubing and membranes, blood oxygenator tubing and membranes, blood bags, sutures, membranes, cell culture devices, chromatographic support materials, biosensors, and the like.

The invention will now be demonstrated referring to the following non-limiting examples.

EXAMPLE 1

Synthesis of N-[3-(7-Methyl-9-oxothioxanthene-3-carboxamido) propyl]methacrylamide (MTA-APMA; Compound 1)

N-(3-aminopropyl)methacrylamide hydrochloride (APMA), 4.53 g (25.4 mmol), prepared as described in U.S. Pat. No. 5,858,653, Example 2, was suspended in 100 ml of anhydrous chloroform in a 250 ml round bottom flask equipped with a drying tube. 7-methyl-9-oxothioxanthene-3-carboxylic acid (MTA) was prepared as described in U.S. Pat. No. 4,506,083, Example D. MTA-chloride (MTA-Cl) was made as described in U.S. Pat. No. 6,007,833, Example 1. After cooling the slurry in an ice bath, MTA-Cl, 7.69 g (26.6 mmol), was added as a solid with stirring. A solution of 7.42 ml (53.2 mmol) of triethylamine (TEA) in 20 ml of chloroform was then added over a 1.5 hour time period, followed by a slow warming to room temperature. The mixture was allowed to stir 16 hours at room temperature under a drying tube. After this time, the reaction was washed with 0.1 N HCl and the solvent was removed under vacuum after adding a small amount of phenothiazine as an inhibitor. The resulting product was recrystallized from tetrahydrofuran (THF)/toluene (3/1) and gave 8.87 g (88.7% yield) of product after air drying. The structure of Compound 1 was confirmed by NMR analysis.

EXAMPLE 2

Synthesis of MTA-PAAm (Compound 2)

MTA-APMA was copolymerized with acrylamide in DMSO in the presence of mercaptoethanol (a chain transfer agent), N,N,N',N'-tetramethylethylenediamine (TEMED; cocatalyst), and 2,2'-azobis(2-methyl-propionitrile)(AIBN; free radical initiator) at room temperature. The solution was sparged with nitrogen for 20 minutes, sealed tightly, and incubated at 55° for 20 hours. The solution was dialyzed for 3 days against deionized (DI) water using continuous flow dialysis. The resultant MTA-PAAm (Compound 2) was lyophilized, stored desiccated, and protected from light at room temperature.

EXAMPLE 3

Synthesis of Polymerizable Hyaluronic Acid (HA; Compound 3)

Two grams of hyaluronic acid (HA; Lifecore Biomedical, Chaska, Minn.) were dissolved in 100 ml of dry formamide. To this solution were added 1.0 g (9.9 mmol) of TEA and 4.0 g (31 mmol) of glycidyl acrylate. The reaction mixture was stirred at 37° C. for 72 hours. After exhaustive dialysis against deionized water using 12-14 k MWCO (Millipore Co. Billerica, Mass.) dialysis tubing, the product, Compound 3, (2.89 grams) was isolated by lyophilization.

EXAMPLE 4

Preparation of Sodium N-vinylsuccinimide-2-sulfonate (NVSS; Compound 4)

N-vinylmaleimide (10.0 g, 81 mmole; as prepared by the procedure in *Macromol. Rapid Commun.* 15, 867-872 (1994)); sodium bisulfite (8.5 g, 82 mmole); and DI water (158 ml) were placed in a flask and stirred at 70° C. for 6 hours. The water solution was lyophilized to give 18.5 g of Compound 4. Analysis by NMR was consistent with the desired product $^1$H NMR (400, $D_2O$), δ (ppm): vinyl proton-7a 6.57 (d of d (=16.28, 9.61), 1H), vinyl proton-8a 5.88 (d (j=16.28), 1H), vinyl proton-8b 5.20 (d (j=9.61), 1H), methyne-4a 4.30 (d of d (j=9.19, 3.35), 1H), methylene-5b 3.22 (d of d (j=19.12, 9.19), 1H), and methylene-5a 3.03 (d of d(j=19.13, 3.35), 1H).

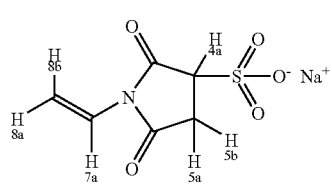

Compound 4

EXAMPLE 5

Preparation of Potassium 3-({3-[formyl(vinyl)amino]propanoyl}oxy)propane-1-sulfonate (NVF-SPA; Compound 5)

The Michael addition of vinylformamide (40 ml, 571 mmole) to potassium 3-(propionyloxy)-propane-1-sulfonate (10 g, 43 mmole) was catalyzed by butyllithium (32 mg, 0.5 mmole). The reaction was stirred at 65° C. for 8 hours. The solution was added to diethyl ether (300 ml) to precipitate the product. The product, Compound 5, was isolated by filtration. Analysis by Liquid Chromotagraphy—Mass Spectrometry (LCMS) was consistent with the predicted molecular weight.

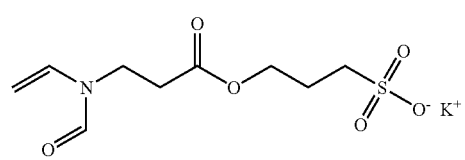

Compound 5

EXAMPLE 6

Preparation of 2-vinyl-2-azabicyclo[2.2.1]hept-5-en-3-one (Compound 6)

A solution of 2-azabicyclo[2.2.1]hept-5-en-3-one (0.5 g, 4.6 mmole) in vinyl acetate (3 ml, 33 mmole) with sodium tetrachloropalladate (15 mg, 0.05 mmole) was refluxed for 5 days. The product, Compound 6, was isolated by evaporation of the volatiles. Analysis by Gas Liquid Chromatography-Mass Spectrometry (GLC-MS) was consistent with the predicted molecular weight.

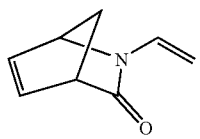

Compound 6

EXAMPLE 7

Preparation of 5,6-dihydroxy-2-vinyl-2-azabicyclo[2.2.1]heptan-3-one (Compound 7)

The intermediate 5,6-dihydroxy-2-azabicyclo[2.2.1]heptan-3-one is made by stirring a solution of 2-azabicyclo[2.2.1]hept-5-en-3-one (1.00 g, 9.16 mmole) and osmium tetroxide (2.33 g, 9.16 mmole) in pyridine (35 ml) at room temperature for 2 hours. The osmate ester is cleaved by mixing the reaction solution with a solution of sodium bisulfite (4.2 g) in water (70 ml) and pyridine (50 ml). The product is extracted from the reaction solution with 3-150 ml portions of methylene chloride. Evaporation of the dried methylene chloride gives the crude dihydroxy bicyclic amide (intermediate). The intermediate is mixed with sodium tetrachloropalladate (30 mg, 0.10 mmole) and vinyl acetate (6 ml, 66 mmole). The mixture is then refluxed for 5 days. The crude product (Compound 7) is isolated by filtration to remove the catalyst and evaporation of the excess vinyl acetate.

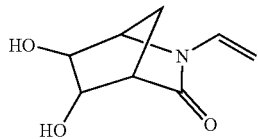

Compound 7

EXAMPLE 8

Evaluation of Matrix Formation Using NVSS (Compound 4)

To evaluate the matrix forming abilities using NVSS, a solution of 3 wt % polymerizable hyaluronic acid (pHA) and 0.3 wt % MTA-PAAm was prepared. To this solution was added 0.2 wt % NVSS; a control solution not including the NVSS was also evaluated (NON). 50 ul of the mixtures containing NVSS and NON were individually placed onto a glass slide and illuminated each for 50 seconds with an EFOS 100 SS illumination system equipped with a 400-500 nm filter (Mississauga, Ontario, Canada). After illumination, the polymer formulations were evaluated for gel formation. The mixture containing NVSS was found to form a very firm gel with elastomeric properties. The mixture containing NON did not form a gel and remained in a liquid state.

EXAMPLE 9

Incorporation of NVSS (Compound 4) into HA Matrices

One set of HA matrices was formed as described in Example 6. Another set of HA matrices was formed substituting N-vinyl-pyrrolidone (NVP) for NVSS. The formed matrices were evaluated by Fourier Transform-Infra Red (FT-IR) spectroscopy utilizing Attenuated Total Reflectance (ATR). A Nicolet 560 Magna FT-IR spectrometer equipped with a SensIR multi-bounce diamond ATR accessory was used for the analysis.

The presence of NVSS(N-vinyl-sulfosuccinimide) in the HA matrices was indicated by the presence of NVSS peaks ($\pm 5$ cm$^{-1}$) at 1236 cm$^{-1}$, 1202 cm$^{-1}$, and 1043 cm$^{-1}$. Furthermore, these peaks were still present in the HA gels after the gels had been washed with water for 60 minutes, which suggested the incorporation of NVSS into the HA gels. The association of these peaks to NVSS was confirmed by the comparison of HA gels with NVSS to HA gels with NVP. As expected, the spectra of the HA gels with NVP revealed the absence of these functional groups in the gels. In the spectra of HA gels with NVP, the 1236 cm$^{-1}$ (C—N—C & C—O stretching in NVSS) and the 1202 cm$^{-1}$ (SO$_3$ stretching in NVSS) peaks were absent, and the 1043 cm$^{-1}$ (SO$_3$ & C—O stretching in NVSS) peak intensity was decreased.

EXAMPLE 10

Test for Viability of Encapsulated Islets

The viability of encapsulated islets is tested by culturing the encapsulated islets in RPMI 1640 (Hyclone, Logan, Utah) with 10% fetal calf serum (FCS) (Hyclone, Logan, Utah) for 48 h and then staining the cultured islets (Warburton and James, "Hemocytometer cell counts and viability studies", *Cell and tissue culture: Laboratory procedures*, (eds) A. Doyle, J. B. Griffiths and D. G. Newell, John Wiley pp 11-15 (1995)), using 0.4% (w/v) trypan blue (ICN Pharmaceuticals, Inc., USA). Blue stained islets are scored as non-viable as compared to the unstained viable islets.

EXAMPLE 11

Test for Encapsulated Islet Functionality

Functionality of the encapsulated pancreatic islet cells is tested by transplantation of islet-capsules into diabetic mice. Male BALB/c mice are rendered diabetic with streptozotocin (STZ; e.g., 200 mg/kg body weight; Sigma Chemicals Co., Dorseth, UK). After fasting overnight the mice are anaesthetized and an encapsulated islet preparation, and a control preparation is introduced into the abdomen of separate animals.

Fasting plasma glucose levels of all the mice containing the transplanted islets are recorded post-transplantation using a using a glucometre (Reflolux/S, Boehrringer Mannheim, Germany) with compatible glucose detection strips (Haemo-Glukotest 20-800 R, Boehrringer Mannheim).

EXAMPLE 12

Test for Encapsulated Islet Biocompatibility

The histopathology of transplanted encapsulated islets is assessed using microscopy and other means to determine the integrity of the encapsulated islets, the extent of fibrotic overgrowth, and the interaction of various cell types including immune or other blood cells.

We claim:
1. A composition comprising:
   (a) a polymerization accelerator comprising a biocompatible functional group, wherein the biocompatible functional group comprises a sulfonate group; and
   (b) a polymerizable material, wherein the polymerization accelerator is able to be reacted with the polymerizable material to form a biocompatible matrix and the polymerization accelerator increases the rate that the polymerizable material becomes incorporated into the biocompatible matrix.
2. A composition comprising:
   (a) a polymerization accelerator comprising a biocompatible functional group selected from the group consisting of phosphonate (PO$_3^-$), sulfonate (SO$_3^-$), and carboxylate (COO$^-$), a carbonyl group, and an N-vinyl group; and
   (b) a polymerizable material, wherein the polymerization accelerator increases the rate that the polymerizable material becomes incorporated into a polymerized product in a polymerization reaction.
3. The composition of claim 2 further comprising a polymerization initiator.
4. The composition of claim 3 wherein the polymerization initiator comprises a photoinitiator group.
5. The composition of claim 4 wherein the photoinitiator group is a long-wave ultra violet- or visible light-activatable molecule.
6. The composition of claim 2 wherein the polymerizable material comprises a macromer.
7. The composition of claim 6 wherein the macromer is selected from the group consisting of water-soluble macromers.

8. The composition of claim 6 wherein the macromer is present at a concentration in the range of 0.5-50 wt %.

9. The composition of claim 8 wherein the macromer is present at a concentration in the range of 1-30 wt %.

10. The composition of claim 1 further comprising an acceptor or reductant that forms a free radical and causes free radical polymerization of the polymerizable material in the polymerization reaction.

11. The composition of claim 2 wherein the biocompatible functional group comprises a sulfonate group.

12. The composition of claim 1 wherein the polymerization accelerator comprises an N-vinyl amide group.

13. The composition of claim 1 wherein the N-vinyl nitrogen is an atom in a heterocyclic ring.

14. The composition of claim 1 wherein the polymerization accelerator is able to react with the polymerizable material to form the polymerized product having biocompatible properties.

15. The composition of claim 1 wherein the polymerization accelerator is present in an amount sufficient to improve the biocompatibility properties of the polymerized product.

16. The composition of claim 1 wherein the polymerization accelerator is present in an amount sufficient to promote formation of the polymerized product.

17. The composition of claim 16 wherein the polymerization accelerator is present at a concentration of 0.05 wt % or greater.

18. The composition of claim 17 wherein the polymerization accelerator is present at a concentration in the range of 0.05-1.0 wt %.

19. The composition of claim 6 wherein the macromer comprises a protein or polyamino acid.

20. The composition of claim 19 wherein the macromer is selected from the group consisting of gelatin, collagen, fibronectin, laminin, albumin, and active peptides thereof.

21. The composition of claim 6 wherein the macromer comprises a polysaccharide.

22. The composition of claim 21 wherein the macromer is selected from the group consisting of hyaluronic acid (HA), starch, dextran, heparin, and chitosan.

23. A composition comprising:
(a) a polymerization accelerator comprising:
   i) a biocompatible functional group selected from the group consisting of phosphonate ($PO_3^-$), sulfonate ($SO_3^-$), and carboxylate ($COO^-$), ii) an N-vinyl group, and iii) a carbonyl group; and
(b) a macromer,
wherein the polymerization accelerator is able to be reacted with the macromer to form a biocompatible matrix and the polymerization accelerator increases the rate that the macromer becomes incorporated into the biocompatible matrix.

24. The composition of claim 23 wherein the biocompatible functional group comprises a sulfonate group.

* * * * *